United States Patent [19]

Vora et al.

[11] Patent Number: 4,712,008
[45] Date of Patent: Dec. 8, 1987

[54] ION MOBILITY SPECTROMETER

[75] Inventors: Kishore N. Vora, Herndon, Va.; John P. Carrico, Sr., Baltimore, Md.; Glenn E. Spangler, Lutherville, Md.; Donald N. Campbell; Charles E. Martin, both of Timonium, Md.

[73] Assignee: Allied Corporation, Morristown, N.J.

[21] Appl. No.: 908,840

[22] Filed: Sep. 18, 1986

[51] Int. Cl.[4] .............................. H01J 49/40
[52] U.S. Cl. ................... 250/287; 250/288; 73/864.81
[58] Field of Search ............. 250/288 A, 287, 286, 250/288, 397, 281; 73/864.81

[56] References Cited

U.S. PATENT DOCUMENTS

| | | | |
|---|---|---|---|
| 3,697,748 | 10/1972 | Cohen | 250/288 |
| 4,311,669 | 1/1982 | Spangler | 422/98 |
| 4,378,499 | 3/1983 | Spangler et al. | 250/287 |
| 4,390,784 | 6/1983 | Browning et al. | 250/287 |
| 4,445,038 | 4/1984 | Spangler et al. | 250/382 |

OTHER PUBLICATIONS

G. E. Spangler et al., "Optimization of a Miniaturized Ion Mobility Spectrometer Cell" 1984 Abstracts, The Pittsburgh Conf. and Exposition on Analytical Chem. and Applied Spectroscopy, Atlantic City, N.J., USA, Mar. 5-9, 1984.

Primary Examiner—Craig E. Church
Assistant Examiner—Jack I. Berman
Attorney, Agent, or Firm—Robert M. Trepp; Bruce L. Lamb

[57] ABSTRACT

An ion mobility spectrometer is described for detecting gas constituents in an ambient air incorporating a cylindrical tube containing a reaction region, a shutter assembly and a drift region therein, the cylindrical tube fits within a housing having a chamber or space between the cylindrical tube and the housing for heating drift gas prior to entry into the drift region. Further, the cylindrical tube may have interior annular ledges to facilitate positioning of the shutter assembly and an aperture grid. The invention overcomes the problem of controlling the temperature of the drift gas prior to entry into the drift region to enhance the uniformity of ion drift mobility times and the problem of a mechanical assembly which is difficult to dissemble.

8 Claims, 8 Drawing Figures

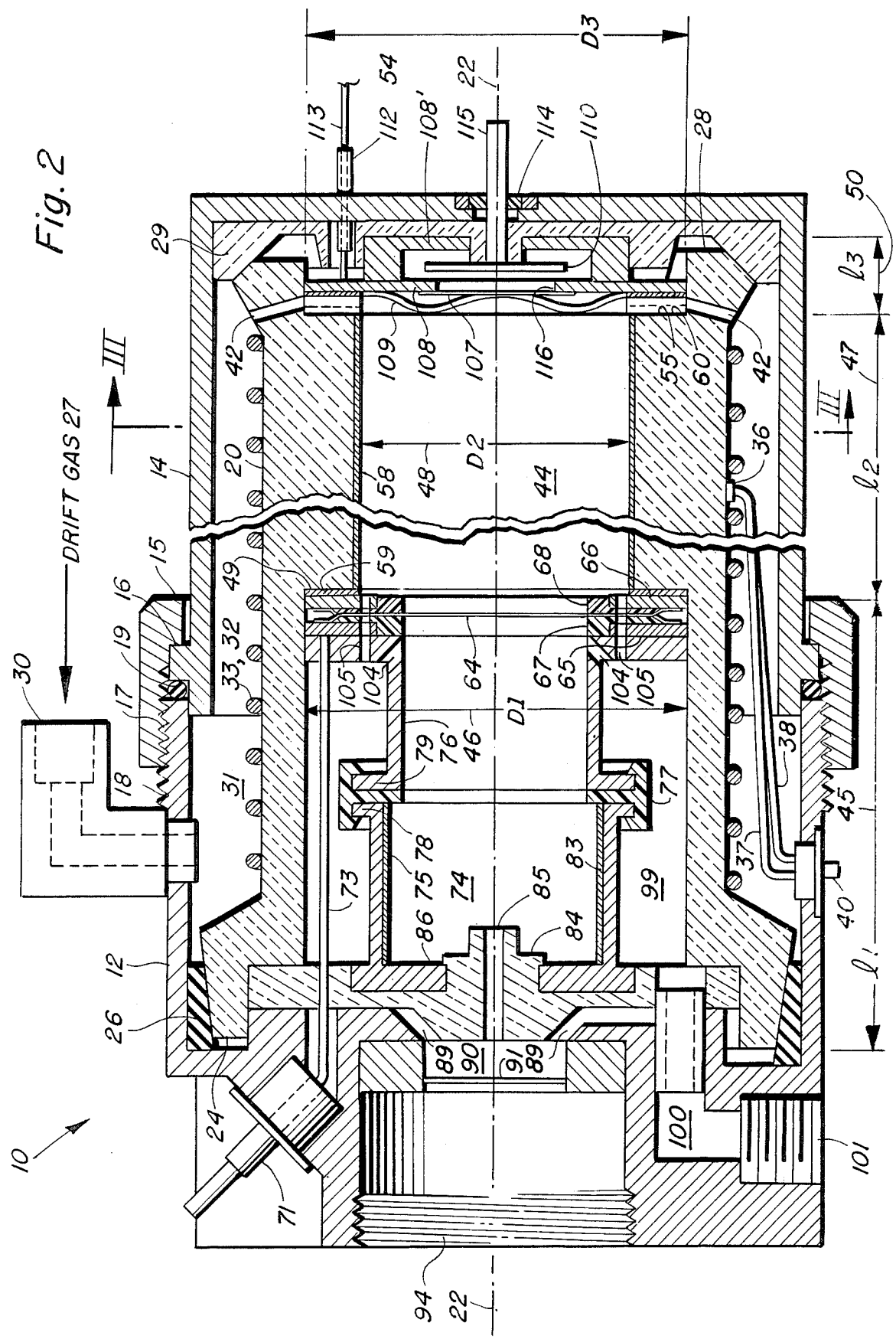

ION MOBILITY SPECTROMETER

Cross Reference to a Related Application

Cross reference is made to U.S. application Ser. No. 701,898 filed on Feb. 15, 1985, entitled "Selective Ionization of Gas Constituents Using Electrolytic Reactions" by K. N. Vora et al. and assigned to the assignee herein which is directed to an electrolytic ionization source using inorganic/organic salts for use in an ion mobility spectrometer, an ionization detector and a mass spectrometer.

BACKGROUND OF THE INVENTION

1. Field of the Invention

This invention relates to ion mobility spectrometers and more particularly to a miniature ion mobility spectrometer.

2. Description of the Prior Art

The technique of ion mobility spectrometry (IMS) was disclosed in the early 1970's in order to analyze and detect organic vapors. A typical ion mobility spectrometer (IMS) detector cell consists of a reaction region for generating ions and a drift region for measuring the mobility of the ions. The reaction region and the drift region are separated by a shutter grid which functions to gate the ions from the reaction region into the drift region. An inlet duct provides a gas to the reaction region. In the reaction region an ionization source, for example, tritium, $63_{Ni}$, $241_{Am}$, etc. ionizes some of the gas. An electric field in the reaction region moves the ions towards the shutter grid. The ions are gated into the drift region where their mobility is measured by their arrival times at a collector at the far end of the drift region. The drift region is biased with an electric field to move the ions towards the collector. The drift region may have a drift gas flowing therein from the collector towards the shutter grid.

One example of a means for providing an electric bias field in the drift region as well as the reaction region is provided in U.S. Pat. No. 4,390,784 which issued on June 28, 1983 to D. R. Browing et al. and assigned to The Bendix Corp., now merged with the assignee herein. In U.S. Pat. No. 4,390,784 a ceramic tube is disclosed with a coating on its inside surface of a thick film resistor. A voltage potential is placed across the film in the longitudinal direction of the drift region to provide a longitudinal electric field from the shutter grid to the collector.

In U.S. Pat. No. 4,445,038 which issued on Apr. 24, 1984 to G. E. Spangler and J. F. Wroten, Jr. and assigned to The Bendix Corporation, now merged with the assignee herein, an ion mobility detector is described having dual drift regions respectively on either side of a centrally located reaction region and respectively separated from the reaction region by dual shuttered grids.

An improvement to the inlet of gas to the reaction region is described in U.S. Pat. No. 4,311,669 which issued on Jan. 19, 1982 to G. E. Spangler entitled "Membrane Interface for Ion Mobility Detector Cells" which is assigned to The Bendix Corporation, now merged with the assignee herein. In U.S. Pat. No. 4,311,669, a membrane interface is provided over the sample inlet port of an ion mobility detector. The sample penetrates the membrane and is carried into the ion mobility detector by means of a carrier gas which scrubs the interior surface of the membrane.

Another improvement to the inlet of gas into the reaction region is described in U.S. Pat. No. 4,378,499 which issued to G. E. Spangler et al. which is assigned to The Bendix Corporation now merged with the assignee herein entitled "Chemical Conversion for Ion Mobility Detectors Using Surface Interactions". In U.S. Pat. No. 4,378,499 the inlet gas including a sample is passed through a catalytic reactive filter prior to injection into the reaction region of an ion mobility spectrometer to enhance selectivity and sensitivity by converting through surface interactions sample gas or vapor to a form more readily ionized or by converting through surface interactions interferent gas or vapor to a form less readily ionized. Alternatively, the inlet gas may be exposed to a reactive coating placed on the surface of a permeable membrane prior to diffusion therethrough into the reaction region or exposed to a reactive coating placed on the interior walls of the reaction region. The reaction region is formed by a plurality of conductive rings and a drift region formed by a plurality of conductive rings with drift gas entering near the detector and being exhausted near the shutter grid.

It is therefore desirable to provide an ion mobility spectrometer which is easy to assemble and miniature in size.

It is further desirable to provide an ion mobility spectrometer which has a metal housing surrounding a conductive inlaid tube (CIT) which provides an electrical and thermal shield to the CIT.

It is further desirable to provide an ion mobility spectrometer with a CIT with heater elements affixed to the outside surface for heating the CIT and for heating the gas entering the drift region.

In is further desirable to provide an ion mobility spectrometer wherein the drift and carrier gases are exhausted through holes in the shutter assembly and the conductive ring adjacent thereto to allow counter-flow of gases in the drift region and to prevent signal degradation as a result of gas mixing and dilution of the carrier gas and drift gas in the reaction region.

It is further desirable in an ion mobility spectrometer to provide an aperture and collector configuration designed as a Faraday shield enclosing the collector so that relative motion between aperture grid and collector is compensated by motion of opposite polarity and that effects of microphonic noise are reduced.

SUMMARY OF THE INVENTION

An apparatus and method is described for detecting gas constituents in ambient air comprising a first housing having a first opening and a reaction region, the first housing having a first means for generating ions in the reaction region, the first housing having a first inlet duct for passing carrier gas to the reaction region, the first housing having a second inlet duct for passing ambient gas to the reaction region, a shutter grid positioned adjacent the reaction region for controlling the passage of ions from the reaction region, a second housing having a second opening mating with the first opening and having a drift region therein for receiving said ions passing said shutter grid at times the first and second openings are mated, means for generating an electric field in the drift region for causing the ions to drift towards a collector plate, an aperture grid positioned between the collector plate and the second opening, means for biasing the aperture at a predetermined potential, means for heating the drift region to a predetermined temperature, the second housing having a third inlet for receiving the drift gas, the third inlet coupled to a duct, the duct positioned in thermal communication with the means for heating the drift region for heating the duct and drift gas therein to a predetermined temperature, the duct having an outlet for flowing the drift gas into the drift region, the first housing having an exhaust duct positioned in the first housing and extending to the shutter grid for removing sample gas and carrier gas from the reaction region and drift gas from the drift region.

The invention further provides an ion mobility spectrometer comprising a cylindrical tube having a longitudinal axis and having a first and second end, the cylindrical tube having a first length from the first end having at least a first internal diameter and a second length extending from the first length towards the second end, having a second internal diameter less than the first internal diameter to provide a first interior annular ledge at the junction of the first and second lengths, and a third length extending from the second length to the second end having a third internal diameter greater than the second internal diameter to provide a second interior annular ledge at the junction of the second and third lengths, a drift region formed by a first conductive layer having a predetermined resistance positioned on the interior surface of the second length of the cylindrical tube for generating an electric field, a second conductive layer having a predetermined resistance positioned on the first and second interior annular ledges and conductively joining the first conductive layer for applying a potential across the first conductive layer, a shutter assembly positioned inside the cylindrical tube transverse to the longitudinal axis having conductive peripheral portions positioned against the first interior annular ledge to provide electrical contact between the shutter assembly and the second conductive layer, a reaction region formed from a plurality of conductive rings insulated from one another and positioned side by side in the first length of the cylindrical tube between the first end and said shutter assembly with at least one passageway between the outside surface of the conductive rings and the interior surface of the first length of the cylindrical tube to permit carrier and drift gases to flow from the shutter assembly to the first end of the cylindrical tube, the first end of the cylindrical tube positioned against a first housing having means for receiving the cylindrical tube to form an air-tight seal, the first housing having an inlet for receiving ambient air, the first housing having a membrane having one side exposed to the received ambient air, the first housing having a carrier gas inlet for receiving carrier gas, including means for passing the carrier gas past the unexposed side of the membrane and into the reaction region, the reaction region having means for generating ions in the reaction region, the reaction region including means for placing a potential on the plurality of conductive rings with respect to the shutter assembly to move the ions toward the shutter assembly, the shutter assembly having means for directing the carrier gas from the reaction region to the at least one passageway between the outside surface of the conductive rings and the interior surface of the first length of the cylindrical tube, the first housing having an outlet duct for exhausting the carrier gas and the drift gas received from the at least one passageway at the first end of the cylindrical tube, an aperture grid positioned inside the third length of the cylindrical tube transverse to the longitudinal axis having conductive peripheral portions positioned against the second interior annular ledge to provide electrical contact between the aperture grid and the second conductive layer, a second housing having means for receiving the second end of the cylindrical tube, the second housing extending from the second end over at least the second length of the cylindrical tube having a space between the second length and the second housing, the second housing having an inlet for receiving drift gas into the space between the second length of the cylindrical tube and the second housing, a duct means for passing the drift gas from said space into the drift region by way of the second end of the cylindrical tube, the cylindrical tube having a heating element fixedly attached to the exterior surface of the cylindrical tube for heating the second length of the cylindrical tube and the drift gas in the space above the cylindrical tube prior to entry into the cylindrical tube, the second housing having a collector positioned behind the aperture grid for collecting ions passing through the aperture grid, means for coupling a bias voltage to the aperture grid, means for coupling a signal from the collector indicative of the ions collected by the collector, and means for coupling power to the heating element.

BRIEF DESCRIPTION OF THE DRAWING

FIG. 2 is a cross section view along the lines II—II of FIG. 1.

DESCRIPTION OF THE PREFERRED EMBODIMENT

Figure 1:
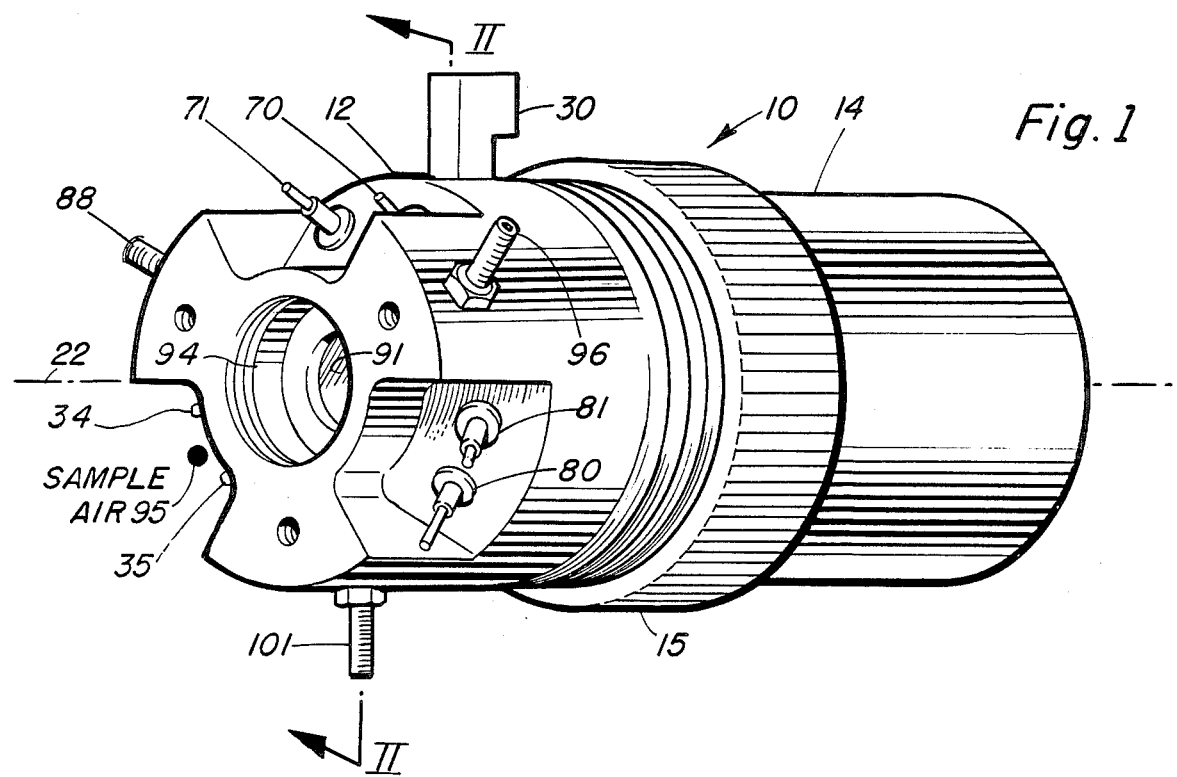
FIG. 1 is a pictorial view of one embodiment of the invention.

Referring to FIGS. 1 and 2, an ion mobility spectrometer 10 is shown. Ion mobility spectrometer 10 has a first housing 12 and a second housing 14 which may be, for example, investment cast aluminum with coatings of tetrafluoroethylene and joined together by a collar 15 which may seat against a flange 16 of second housing 14. Collar 15 may contain threads 17 which may be threaded on threads 18 of first housing 12. A gasket or O ring 19 is positioned between matching surfaces of housings 12 and 14 to provide an airtight seal at times collar 15 is threaded tightly on threads 18. Alternate means of providing an airtight seal may be provided by matching flanges with a gasket or 0 ring placed between and fastended with screws or bolts to tighten the flanges together.

A cylindrical tube 20 having a longitudinal axis 22 is positioned in housing 12 and 14. Cylindrical tube 20 may be, for example, an insulator made from a machinable ceramic such as Macor described in a 1974 Technical Data Sheet AX-3000 from Duramic Products, Inc.

of Pallisades Park, N.J. Cylindrical tube 20 may also be made from alumina, mullite which is a high aluminum oxide/silicon dioxide material, ceramics, quartz, magnesium oxide, glass, etc. Tube 20 may be positioned at its first end 24 by a gasket seal 26 which fits between housing 12 and the outside edge of tube 20. Gasket seal 26 forms an airtight joint between tube 20 and housing 12 at the first end 24 of tube 20. Alternate means of positioning tube 20 in housing 12 may be used to form an air-tight seal between tube 20 and housing 12 at first end 24.

A second end 28 of tube 20 is positioned against insulation material 29 which is supported by housing 14. Inlet 30 is coupled to first housing 12 for coupling drift gas 27 into the space or region 31 between cylindrical tube 20 and housing 12 and 14. The space or volume 31 for holding drift gas 27 between cylindrical tube 20 and housing 12 and 14 includes a heating element 32 which may be, for example resistive wire, for example an alloy of nickel and chromium, wound around the external surface of cylindrical tube 20. Wire 33 may have its ends coupled through low conductive leads to terminals 34 and 35 for attachment to a power source which may be, for example, a power supply 130 shown in FIG. 8. The temperature of space 31 may be, for example, controlled by a temperature sensor 36 which may be, for example, a thermocouple which is coupled over leads 37 and 38 to terminals 39 and 40 mounted in housing 12. Terminals 39 and 40 may be coupled to a heat control circuit 131 shown in FIG. 8, such as a thermostat for controlling the power supplied to terminals 34 and 35 from power supply 130 for maintaining the temperature in space 31 constant. This temperature may be in the range from 25° to 200° C. with a tolerance of plus or minus 1° C. for typical operation.

Several passageways 42 shown in FIG. 2 around or through the periphery of cylindrical tube 20 and near end 28 permit drift gas 27 in space 31 to flow to the indside of cylindrical tube 20. Passageways 42 may be provided in insulation material 29 and washers 108 and 108' to permit drift gas 27 to flow into drift region 44 within cylindrical tube 20.

Cylindrical tube 20 has a first length L1 shown by arrow 45 from first end 24 having at least a first internal diameter D1 shown by arrow 46. Cylindrical tube 20 has a second length L2 shown by arrow 47 extending from the first length shown by arrow 45 towards second end 28 and having a second internal diameter D2 shown by arrow 48. The diameter D2 is less than the diameter D1 to provide a first interior annular ledge 49 at the junction of the first and second lengths of cylindrical tube 20. Cylindrical tube 20 has a third length extending from the second length shown by arrow 50 to second end 28, having an internal diameter D3 shown by arrow 54, which is greater than the internal diameter of the second length shown by arrow 48 to provide a second interior annular ledge 55 at the junction of the second and third lengths of cylindrical tube 20. The first, second and third lengths shown by arrows 45, 47 and 50, respectively, may have inside diameters which are concentric about longitudinal axis 22.

The second length of cylindrical tube 20, shown by arrow 47 has a conductive layer 58 deposited on its inside surface having a predetermined resistance for generating an electric field in the direction of longitudinal axis 22 in drift region 44. Conductive layers 59 and 60 having a low resistance are positioned on first and second annular ledges 49 and 55, respectively, and are conductively joined to conductive layer 58 to provide a low impedance electrical contact for applying a potential across conductive layer 58.

Conductive layers 59 and 60 may be platinum, gold, silver, or copper (in some applications) or alloys thereof. Resistive layer 58 may be a thick film applied in a relatively liquid state and fired to form the resistive layer. Resistive layer 58 may be from thick film resistor material sold, for example by E. I. DuPont de Nemours & Co., Inc. under the tradename BIROX, 9600 series resistor composition. The 9600 series resistor is a glass fritted resistance material which upon firing forms a resistor with a glass-like surface which is relatively hard, impervious to gas and easily cleaned.

Shutter assembly 64 which may be, for example, comprised of two washers 65 and 66 having wires 69 mounted thereon across the center opening, washers 65 and 66 are insulated from one another by annular rings 67 and 68, respectively. Wires 69 are positioned to form a grid of parallel wires alternating from each respective washer with each wire welded to a respective washer. Shutter assembly 64 is positioned inside cylindrical tube 20 transverse to longitudinal axis 22 and having conductive peripheral portions positioned against annular ledge 49 to make electrical contact with conductive layer 59. Terminals 70 and 71 are positioned in housing 12 for coupling voltages therethrough and over leads 72 and 73 to washers 65 and 66, respectively which may be metal, for example stainless steel.

A reaction region 74 is formed from a plurality of conductive rings 75 and 76 positioned in the first length of cylindrical tube 20 between end 24 and shutter assembly 64. Rings 75 and 76 are positioned side by side and supported and insulated from one another by insulating ring 77 which may be made of tetrafluoroethylene (TFE), for example, and has annular recesses for receiving circular flanges 78 and 79 of conductive rings 75 and 76. The annular recesses of insulating ring 77 may be adjusted to permit flanges 78 and 79 to be inserted therein by mechanical pressure. Insulating ring 77 may also provide a seal to contain carrier gas 87 in conductive rings 75 and 76. Terminals 80 and 81 shown in FIG. 1 positioned in housing 12 provide a means for connecting leads thereto and to conductive rings 75 and 76, respectively. A potential may be placed on conductive rings 75 and 76 with respect to shutter assembly 64 to move ions generated in reaction region 74 towards shutter assembly 64. A means for generating ions in reaction region 74 may be provided by a radioactive source such as nickel 63 which may be in the form of a foil 83 and placed on the inside surface of ring 75. Ring 75 is supported and insulated with respect to cylindrical tube 20 by washer 84 which may be, for example, tetrafluoroethylene (TFE). Washer 84 has a passageway 85 through the center thereof for passing carrier gas 87 and sample gas 95 into reaction region 74 from cavity 90. Washer 84 has an annular recess for receiving flange 86 of ring 75 which may be inserted by mechanical pressure and seals ring 75 to washer 84.

Terminals 34, 35, 39, 40, 70, 71, 80 and 81 may contain vacuum feedthroughs of the glass to metal ceramic to metal type in first housing 12. Feedthroughs 112 and 114 may also contain vacuum feedthroughs in second housing 14.

First housing 12 has a carrier gas inlet 88 shown in FIG. 1 for receiving carrier gas 87. Carrier gas inlet 88 is coupled to passageways 89 in first housing 12 for coupling carrier gas 87 to cavity 90 and passageway 85.

Cavity 90 has a membrane 91 over a portion of its surface for introducing sample gas 95 through the membrane. The other side of membrane 91 is exposed to ambient air 95 or sample air 95 through opening 94. An ambient air outlet 96 shown in FIG. 1 may be provided through first housing 12 to facilitate circulation of ambient air or sample gas 95 over membrane 91.

Drift gas 27 entering drift region 44 is vented through passageways 105 in shutter assembly 64 into the space or passageway 99 positioned between the outside surface of conductive rings 75 and 76 and insulating ring 77 and the interior surface of the first length of cylindrical tube 20. Space 99 is coupled through passageway 100 in first housing 12 to outlet duct 101 for exhausting the drift gas 27 and carrier gas 87 from space 99. Reaction region 74 receives carrier gas 87 and sample gas 95 through passageway 85 which may be vented by means of passageway 104 in conductive ring 76 into space 99.

Figure 3:
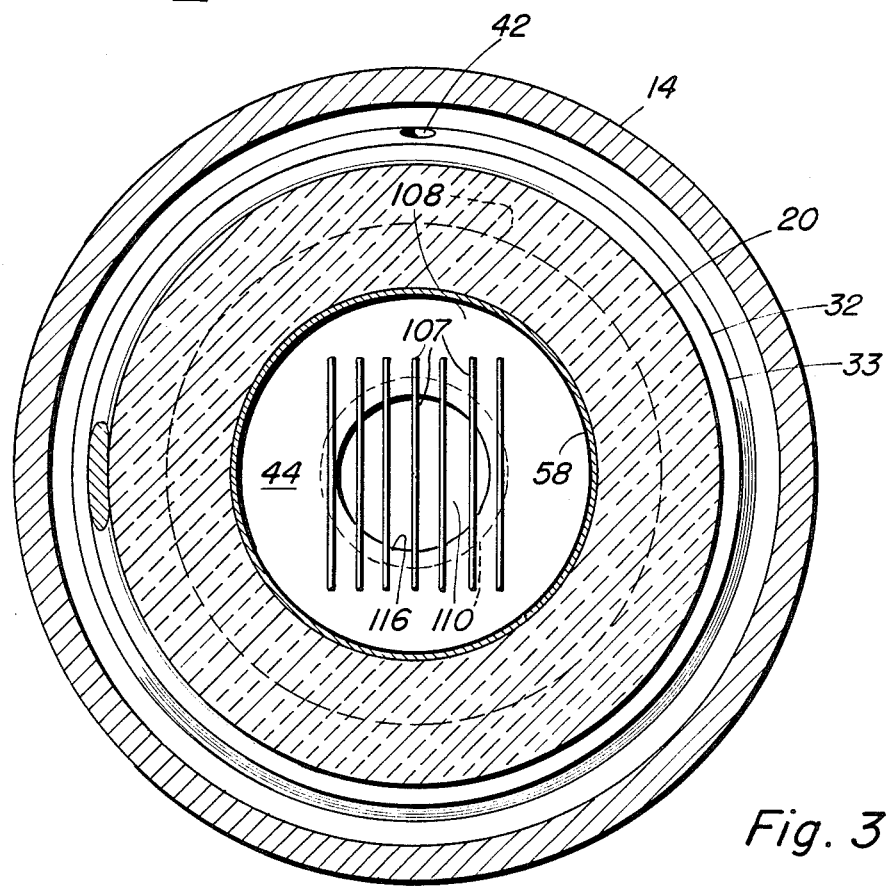
FIG. 3 is a cross section view along the lines III—III of FIG. 2 to show the aperture grid and collector.
Figure 4:
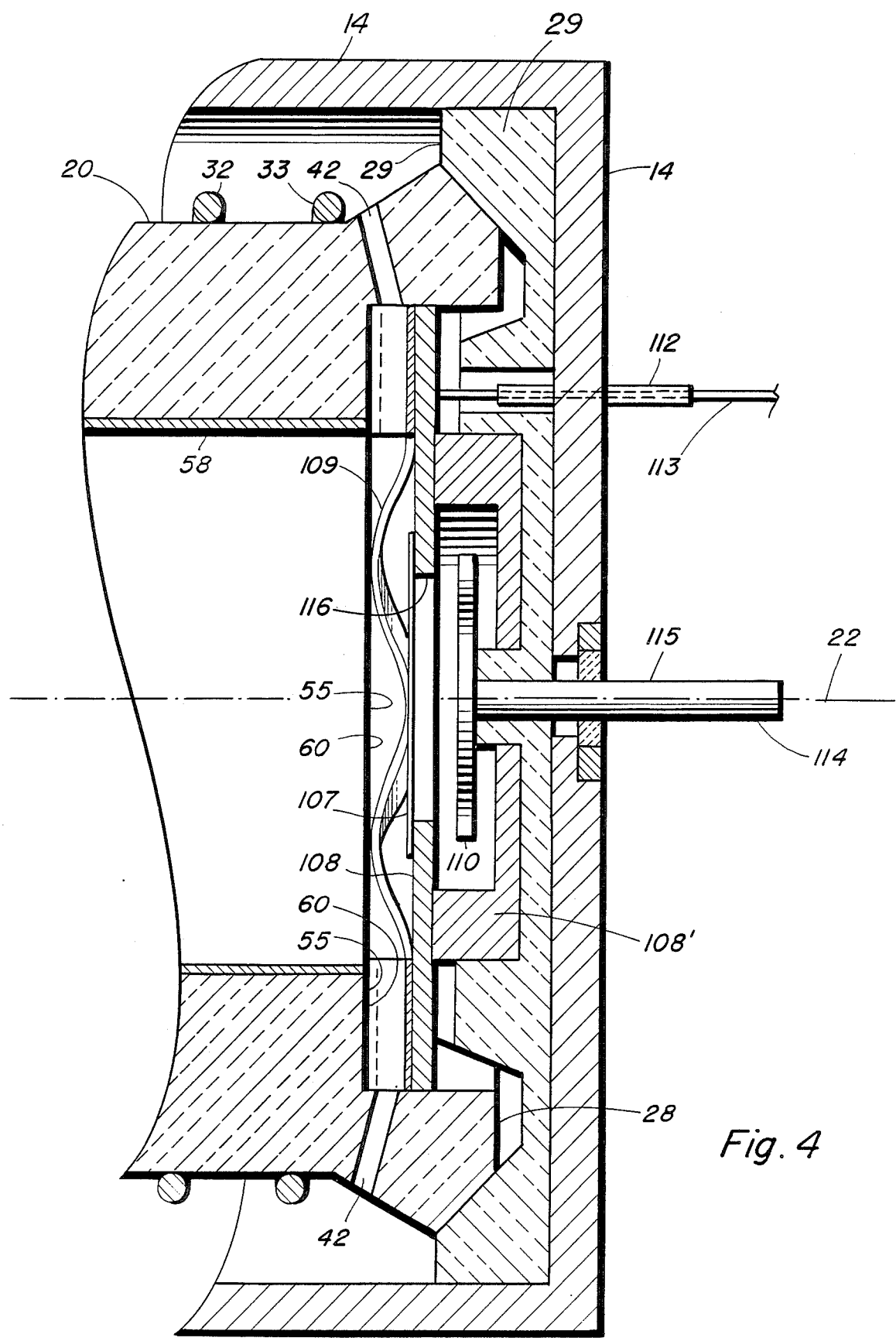
FIG. 4 is an enlarged cross section view of a portion of of FIG. 2.

An aperture grid 107 which may be positioned on a washer 108 is shown in FIGS. 2, 3 and 4 and functions along with washer 108' to provide an electrostatic shield with respect to collector 110. Washer 108 may have a diameter for fitting inside the third length of cylindrical tube 20 against spring washer 109 and annular ledge 55. Washer 108 may be a metal, for example stainless steel or have conductive portions thereon to make electrical contact with conductive layer 60. Feedthrough 112 in second housing 14 permits electrical contact over lead 113 to washers 108 and 108'. Collector 110 is positioned behind aperture grid 107 for collecting ions passing through aperture grid 107 from drift region 44. Feedthrough 114 and lead 115 provide electrical contact to collector 110. Collector 110 may be mechanically supported by lead 115 which may be large in diameter or may be supported by insulation material 29.

Referring to FIG. 3, a plan view of aperture grid 107 and collector 110 is shown. Grid 107 may be comprised of wires for example of stainless steel which may be welded on either side of aperture 116 on washer 108 after having been stretched across. Washers 108 and 10840 may be, for example, two pieces of stainless steel material, respectively, to permit insertion of collector 110..

FIG. 4 is an enlarged cross-section view of a portion of FIG. 2 showing in more detail the electrostatic shielding of washers 108, 108' and grid 107 with respect to collector 110. In FIG. 4, grid 107 and washers 108 and 108' provide electrostatic shielding, a Faraday shield, on all of collector 110 sides except where lead 115 couples to collector 110.

Figure 5:
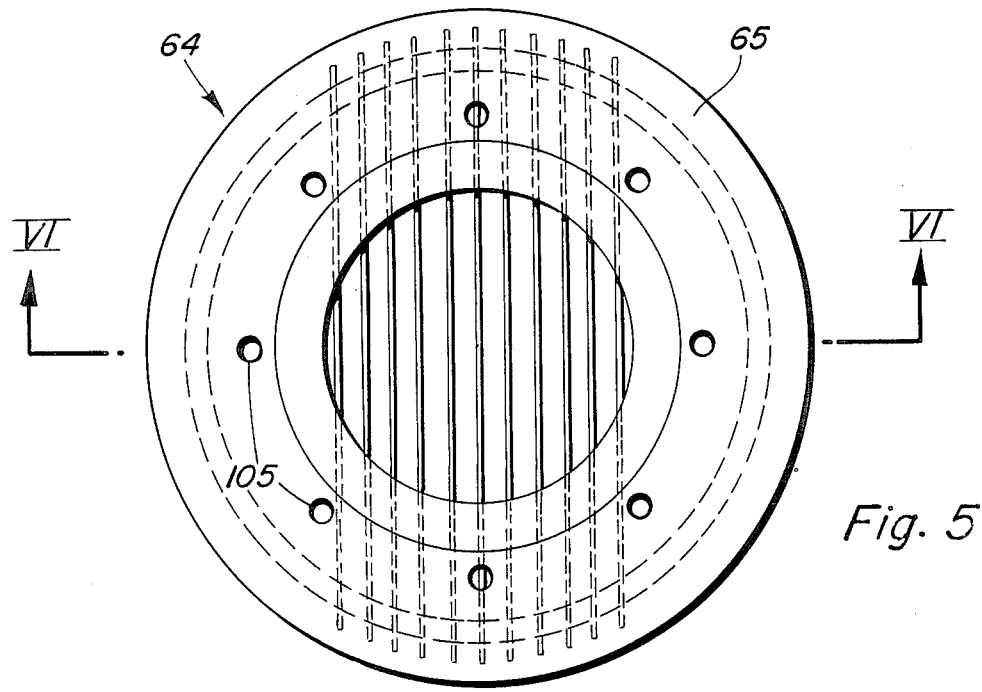
FIG. 5 is a plan view of a shutter assembly suitable for use in FIG. 1.
Figure 6:
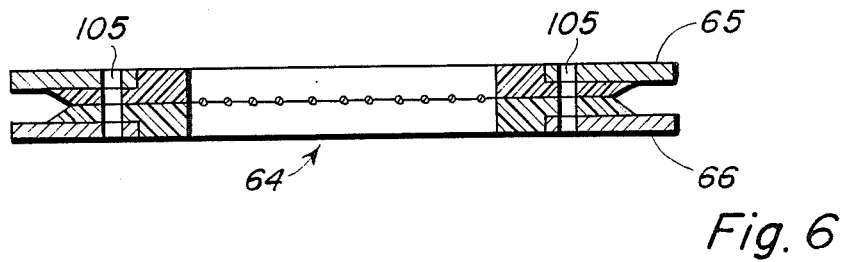
FIG. 6 is a cross section view along the lines VI—VI of FIG. 5.

Referring to FIG. 5, a plan view of shutter assembly 64 is shown. Washer 66 has a diameter slightly less than D1 to permit insertion in the first length of cylindrical tube 20. Washer 66 is conductive or has electrical contacts at its periphery for making electrical contact with conductive layer 59 or annular ledge 49. Annular rings 67 and 68 may be made of TFE. FIG. 6 shows a cross section view of shutter assembly 64 along the lines VI—VI of FIG. 5.

Figure 7:
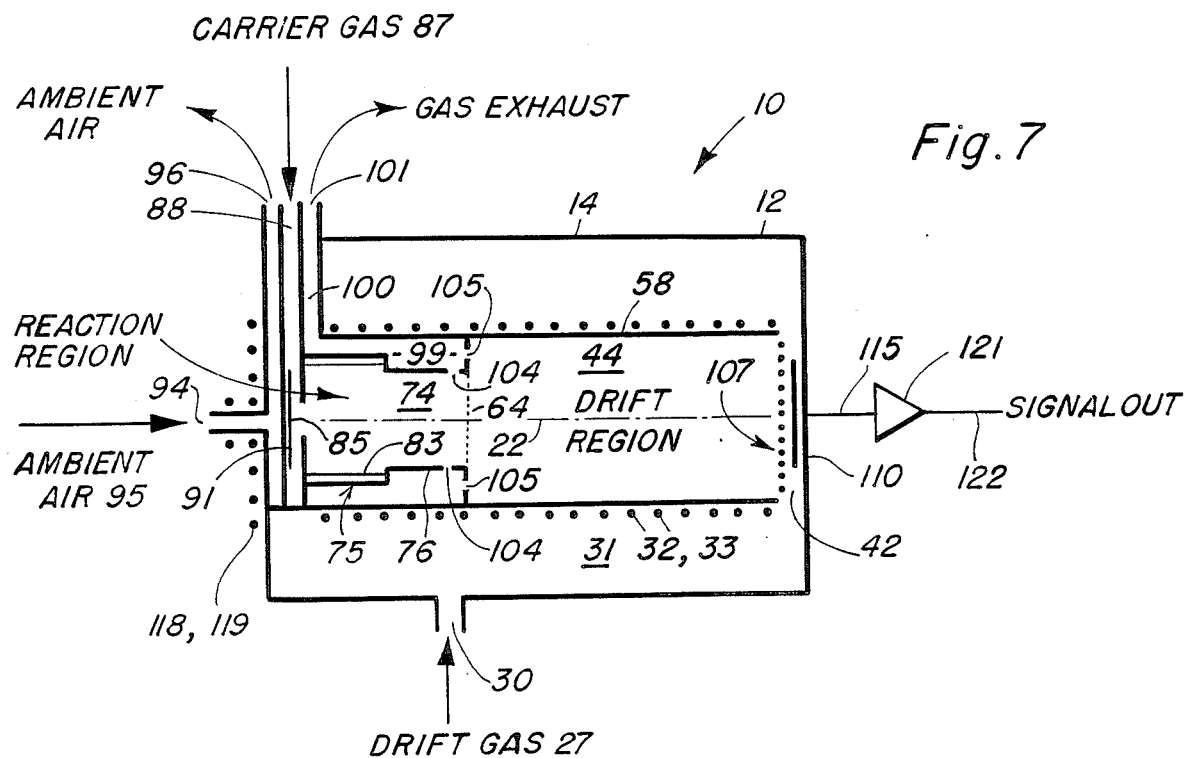
FIG. 7 is a schematic diagram of the embodiment in FIG. 1.

FIG. 7 is a schematic diagram of the embodiment in FIG. 1 of ion mobility spectrometer 10. In FIG. 5, heating element 118 has been added for heating ambient air 95 prior to exposure to membrane 91. Heating element 118 may consist of wires 119 which may be, for example, an alloy of nickel chromium with an insulated coating. A preamplifier 121 is also shown having an input coupled to lead 115 and an output coupled to lead 122. Preamplifier 121 functions to amplify the signal on lead 115.

In operation of ion mobility spectrometer 10, drift gas 27 flows through inlet 30 into space 31. Drift gas 27 is heated to a predetermined temperature by heating element 32 prior to passing into drift region 44 by way of passageways 42. Heating element 32 also functions to heat cylindrical tube 20 and drift region 44. Drift gas 27 after flowing through drift region 44 exits drift region 44 by way of passageways 105 to space 99, passageway 100 and outlet duct 101. Likewise, carrier gas 87 after flowing through reaction region 74 exits reaction region 74 by way of passageways 104 to space 99, passageway 100 and outlet duct 101.

Carrier gas 87 enters carrier gas inlet 88 and passes by or scrubs membrane 91 prior to entering reaction region 74. Ambient air 95 enters opening 94 wherein certain constitutents may pass through membrane 91 into carrier gas 87. Ambient air 95 may be circulated from opening 94 to outlet 96 past the exposed surface of membrane 91. Radioactivity in reaction region 74 generates ions from the carrier gas and constituents of the sample gas or ambient air 95. Electric potentials on conductive rings 75 and 76 and shutter assembly 64 generates an electric field in reaction region 74 which moves ions generated in reaction region 74 towards shutter assembly 64. At an appropriate time shutter assembly 64 is pulsed allowing the ions at shutter assembly 64 to pass therethrough into drift region 44. A conductive layer 58 on the inside of cylindrical tube 20 has an electric potential applied between shutter assembly 64 which may be, for example, 600 v. and aperture grid 107 which may be, for example, 50 v. The potential across conductive layer 58 generates an electric field in drift region 44 which causes ions in drift region 44 to migrate to aperture grid 107 and through aperture grid 107 to collector 110. Collector 110 may be at a potential of virtual or floating ground potential. The ions collected at collector 110 are amplified by preamplifier 121 to provide a signal on line 122. The time of arrival of ions at collector 110 with respect to the pulsing of shutter assembly 64 and the quantity of current is an indication of gas constituents passing through membrane 91 from ambient air 95. The preheating of drift gas 27 prior to entering drift region 44 provides more uniform and predictable measurements in drift region 44 of the time for ions to reach collector 110. Annular ledges 49 and 55 shown in FIG. 2 provide a convenient means of applying a uniform potential across conductive layer 58 to form an electric field parallel to longitudinal axis 22 in drift region 44.

Typical voltages in reaction region 74 which are dependent upon the dimensions in the reaction region may be, for example 850 v., at conductive ring 75. Conductive ring 76 may be at a potential of 700 v. One grid of shutter assembly 64, for example, washer 65 may be at 630 v. and washer 66 may be at 600 v. The polarity of the voltage is dependent upon the polarity of the ions desired to be detected. First housing 12 and second housing 14 may be at 0 v. or ground potential.

Collector 110 is electrostatically isolated from ions in drift region 44 by aperture grid 107. Collector 110 is also surrounded by conductive material as shown in FIG. 4 to further provide electrostatic isolation or a Faraday cage or shield for collector 110 to prevent capacitive coupling to collector 110 of ions in drift region 44 prior to passing through aperture grid 107.

Figure 8:
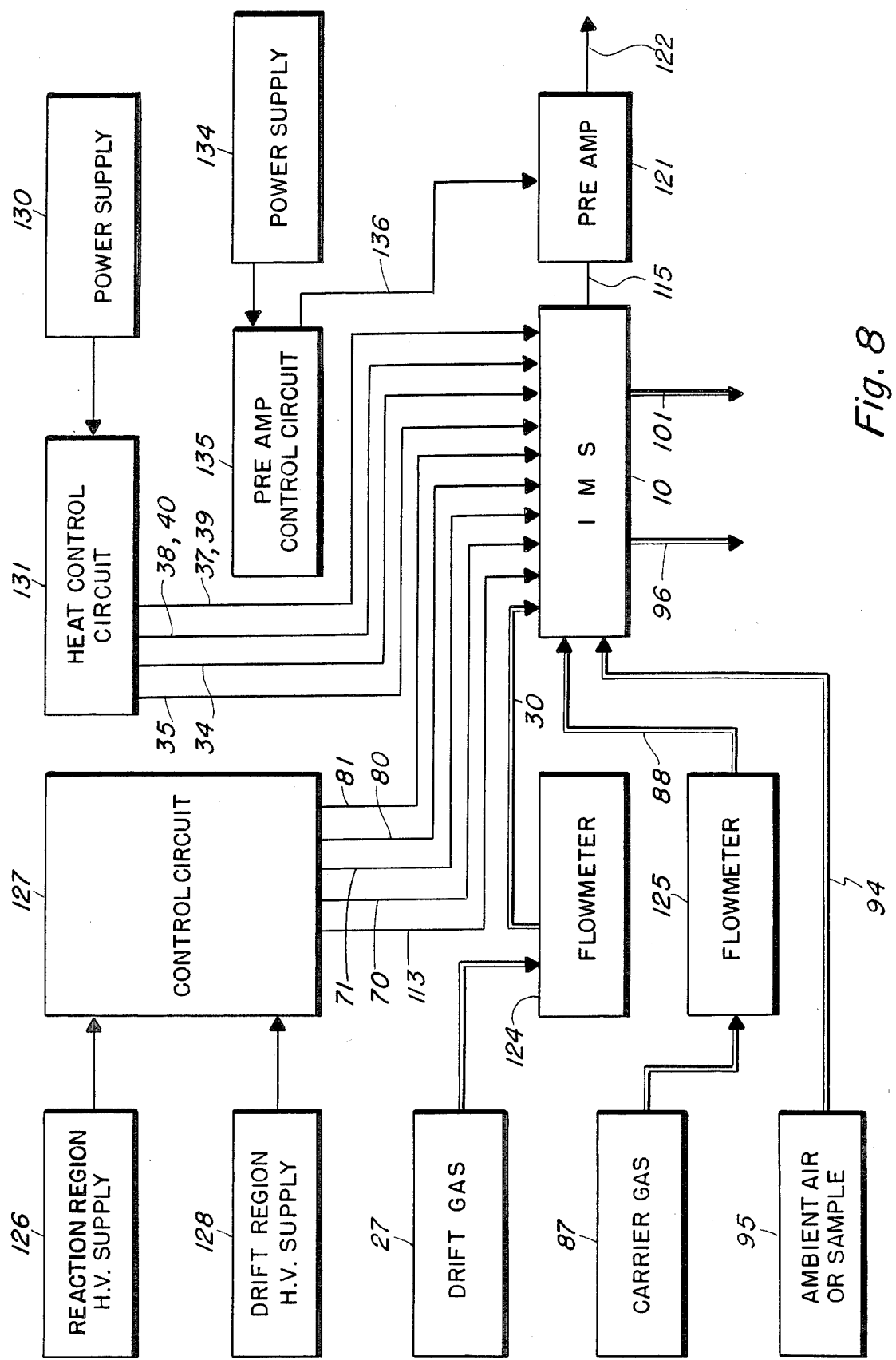
FIG. 8 is a block diagram of FIG. 1 showing additional apparatus connected thereto for typical operation.

FIG. 8 is a block diagram showing peripheral circuits and apparatus coupled to ion mobility spectrometer 10 for typical operation. Drift gas 27 is shown coupled through flow meter 124 to inlet 30. Carrier gas 87 is coupled through flow meter 125 to carrier gas inlet 88. Ambient air or sample 95 is coupled to opening 94. Reaction region high voltage supply 126 is coupled to control circuit 127. Drift region high voltage supply 128 is coupled to control circuit 127. Control circuit 127 functions to apply appropriate voltages to leads 70, 71, 80, 81 and 113. Power supply 130 is coupled to an input of heat control circuit 131. Heat control circuit 131 functions to respond to temperature sensor 36 over leads 37 and 38 to supply power to terminals 34 and 35. Power supply 134 is coupled to an input of preamp control circuit 135. The output of preamp control circuit 135 is coupled over lead 136 to preamplifier 121. Preamp control circuit 135 functions to provide appropriate power supply voltages to preamplifier 121.

An ion mobility spectrometer 10 has been described comprising a housing 12 and 14, a cylindrical tube 20 having a space 31 between portions of the housing 12 and 14 and the cylindrical tube 20 for receiving drift gas 27 which may be preheated in the space 31 prior to entering a drift region 44 which is inside the cylindrical tube 20. A reaction region 44 is also located inside the cylindrical tube adjacent the drift region with a shutter assembly 64 therebetween. The drift gas 27 may be preheated by resistive wire 33 wound around the cylindrical tube 20 with current to the heating element 32 controlled by a thermostat 131 having a sensing element 36 in the space 31 where the drift gas 27 is preheated. The heating element 32 also functions to heat the cylindrical tube 20 and the drift region 74 within the cylindrical tube 20.

The invention further provides an ion mobility spectrometer 10 wherein the reaction region 74 and drift region 44 of the ion mobility spectrometer 10 is positioned within a cylindrical tube 20 having various inside diameters to provide interior annular ledges 49 and 55 for defining the drift region 44. The drift region 44 may have an inside coating 58 on the cylindrical tube 20 of resistive material to provide an electric field in the drift region 44 and the annular ledges 49 and 55 may have a conductive coating for applying a potential to the resistive layer and for receiving a shutter assembly 64 at annular ledge 49 and aperture grid 107 at annular ledge 55.

The invention further provides an ion mobility spectrometer 10 which may be easily assembled and disassembled comprising a cylindrical tube 20 having a first length of at least a first diameter and a second length adjacent the first length of a second diameter, less than the first inside diameter and a third length adjacent the second length having a third diameter greater than said second diameter to provide a first annular ledge 49 between the first and second lengths and a second annular ledge 55 between the second and third lengths. The second length of cylindrical tube 20 having a resistive coating 58 thereon of a predetermined resistance for providing an electric field in the second length parallel with the longitudinal axis 22 of cylindrical tube 20 at times a potential is applied between first and second interior annular ledges 49 and 55, first and second interior annular ledges 49 and 55 having a low impedance conductive layer 59 and 60, respectively thereon in contact with resistive layer 58 for applying a potential across resistive layer 58, a shutter assembly 64 is positioned adjacent the first interior annular ledge 59 in the first length, a reaction region 74 comprising a plurality of conductive rings 75 and 76 having an outside diameter less than the inside diameter of the first length positioned between shutter assembly 64 and the first end 24 of cylindrical tube 20, an aperture grid 107 positioned against second interior annular ledge 55, a collector 110 positioned behind aperture grid 107, a housing 12 and 14 for enclosing cylindrical tube 20 having a means for separating housing 12 and 14 into first and second parts for insertion of cylindrical tube 20, housing 12 and 14 having means for seating first end 24 of said cylindrical tube 20 to form an air seal, housing 12 and 14 having means for introducing a carrier gas 87 and sample gas 95 into reaction region 74, housing 12 and 14 having means for introducing a drift gas 27 into space 31 between housing 12 and 14 and outside portion of cylindrical tube 20, means for heating drift gas 27 in space 31 between cylindrical tube 20 and housing 12 and 14, means for introducing drift gas 27 into drift region 44, and means for exhausting carrier gas 87 and sample gas 95 from reaction region 74 via passageways 104 in conductive ring 76 and drift gas 27 from drift region 44 via passageways 105 in shutter assembly 64, housing 14 having means for seating second end 28 of cylindrical tube 20 and for supporting collector 110.

The invention claimed is:

1. An ion mobility spectrometer comprising a cylindrical tube containing a reaction region, a shutter assembly, a drift region, an aperture grid, and collector; a housing including means for inserting said cylindrical tube therein and having a space between said side walls of said housing and the outside surface of said cylindrical tube, an inlet in said housing for introducing drift gas into said space, a heating element in said space for heating said cylindrical tube and said drift gas and means for introducing said drift gas from said space into said drift region, said cylindrical tube having a first length having at least a first inside diameter and a second length having a second inside diameter less than said first inside diameter forming a first interior annular ledge between said first and second lengths, said ledge having a first conductive layer thereon, the inside surface of said second length having a resistive layer thereon and in electrical contact with said first conductive layer, a shutter assembly positioned against said first interior annular ledge having electrical contacts at its periphery in contact with said first conductive layer on said first interior annular ledge.

2. The ion mobility spectrometer of claim 1 wherein said drift region is formed between said shutter assembly and an aperture grid positioned at the end of said second length.

3. The ion mobility spectrometer of claim 1 wherein said cylindrical tube has a third length having a third diameter greater than said second diameter and adjacent thereto to form a second interior annular ledge.

4. The ion mobility spectrometer of claim 3 wherein said second interior annular ledge has a second conductive layer thereon and said aperture grid has conductive portions in contact with said second conductive layer.

5. The ion mobility spectrometer of claim 4 wherein a collector is positioned adjacent said aperture grid for receiving ions in said drift region from said shutter assembly.

6. The ion mobility spectrometer of claim 5 wherein said aperture grid has conductive portions surrounding said collector to form an electrostatic shield with respect to said collector.

7. An ion mobility spectrometer comprising
a cylindrical tube having a longitudinal axis and having a first and second end, said cylindrical tube having a first length from said first end having at least a first internal diameter and a second length extending from said first length towards said second end having a second internal diameter less than said first internal diameter to provide a first interior annular ledge at said junction of said first and second lengths, and a third length extending from said second length to said second end having a third internal diameter greater than said second internal diameter to provide a second interior annular ledge at said junction of said second and third lengths, a drift region formed by a first conductive layer having a predetermined resistance positioned on the interior surface of said second length of said cylindrical tube for generating an electric field, a second conductive layer having a predetermined resistance positioned on said first and second interior annular ledges and conductively joining said first conductive layer for applying a potential across said first conductive layer, a shutter assembly positioned inside said cylindrical tube transverse to said longitudinal axis having conductive peripheral portions positioned against said first interior annular ledge interior to provide electrical contact between said shutter assembly and said second conductive layer, a reaction region formed from a plurality of conductive rings insulated from one another and positioned side by side in said first length of said cylindrical tube between said first end and with said shutter assembly, at least one passageway between the outside surface of said conductive rings and the interior surface of said first length of said cylindrical tube to permit carrier and drift gases to flow from said shutter assembly to said first end of said cylindrical tube, said first end of said cylindrical tube positioned against a first housing having means for receiving said cylindrical tube to form an air-tight seal, said first housing having an inlet for receiving ambient air, said first housing having a membrane having a first side exposed to said received ambient air, said first housing having a membrane having a first side exposed to said received ambient air, said first housing having a carrier gas inlet for receiving carrier gas, including means for passing said carrier gas past a second side of said membrane and into said reaction region, said reaction region having means for generating ions in said reaction region, said reaction region including means for placing a potential on said plurality of conductive rings with respect to said shutter assembly to move said ions towards said shutter assembly, said shutter assembly having means for directing said carrier gas from said reaction region to said at least one passageway between said outside surface of said conductive rings and said interior surface of said first length of said cylindrical tube, said first housing having an outlet duct for exhausting said carrier gas and the drift gas received from said at least one passageway at said first end of said cylindrical tube, an aperture grid positioned inside said third length of said cylindrical tube transverse to said longitudinal axis having conductive peripheral portions positioned against said second interior annular ledge to provide electrical contact between said aperture grid and said second conductive layer, a second housing having means for receiving said second end of said cylindrical tube, said second housing extending from said second end over at least said second length of said cylindrical tube having a space between said second length and said second housing, said second housing having an inlet for receiving drift gas into said space between said second length of said cylindrical tube and said second housing, said second housing having a duct for passing said drift gas into said drift region by way of said second end of said cylindrical tube, said cylindrical tube having a heating element fixedly attached to said exterior surface of said cylindrical tube for heating said second length of said cylindrical tube and said drift gas in said space outside said cylindrical tube prior to entry into said drift region, said second housing having a collector positioned behind said aperture grid for collecting ions passing through said aperture grid, means for coupling a bias voltage to said aperture grid, means for coupling a signal external of said second housing indicative of said ions collected by said collector, and means for coupling power to said heating element.

8. An ion mobility spectrometer comprising
a cylindrical tube having a longitudinal axis and having a first and second end, said cylindrical tube having a first length from said first end having at least a first internal diameter and a second length extending from said first length towards said second end having a second internal diameter less than said first internal diameter to provide a first interior annular ledge at said junction of said first and second lengths, and a third length extending from said second length to said second end having a third internal diameter greater than said second internal diameter to provide a second interior annular ledge at said junction of said second and third lengths, a drift region formed by a first resistive layer having a predetermined resistance positioned on the interior surface of said second length of said cylindrical tube for generating an electric field, first and second conductive layers positioned on said first and second interior annular ledges respectively and conductively joining said first resistive layer for applying a potential across said first resistive layer, a shutter assembly positioned inside said cylindrical tube transverse to said longitudinal axis having conductive peripheral portions positioned against said first interior annular ledge to provide electrical contact between said shutter assembly and said first conductive layer, a reaction region formed from a plurality of conductive rings insulated from one another and positioned side by side in said first length of said cylindrical tube between said first end and with said shutter assembly, at least one passageway between the outside surface of said conductive rings and the interior surface of said first length of said cylindrical tube to permit carrier and drift gases to flow from said shutter assembly to said first end of said cylindrical tube, said first end of said cylindrical tube positioned against a first housing having means for receiving said cylindrical tube to form an air-tight seal, said first housing having an inlet for receiving ambient air, said first housing having a membrane having a first side exposed to said received ambient air, said first housing having a carrier gas inlet for receiving carrier gas, including means for passing said carrier gas past a second side of said membrane and into said reaction region, said reaction region having means for generating ions in said reaction region, said reaction region including means for placing a potential on said plurality of conductive rings with respect to said shutter assembly to move said ions towards said shutter assembly, means for directing said carrier gas from said reaction region to said at least one passageway between said outside surface of said conductive rings and said interior surface of said first length of said cylindrical tube, said first housing having an outlet duct for exhausting said carrier gas and the drift gas, received from said at least one passageway, at said first end of said cylindrical tube, an aperture grid positioned inside said third length of said cylindrical tube transverse to said longitudinal axis having conductive peripheral portions positioned against said second interior annular ledge to provide electrical contact between said aperture grid and said second conductive layer, a second housing having means for receiving said second end of said cylindrical tube, said second housing extending from said second end over at least said second length of said cylindrical tube having a space between said second length and said second housing, said second housing having an inlet for receiving drift gas into said space between said second length of said cylindrical tube and said second housing, duct means for passing said drift gas into said drift region, said cylindrical tube having a heating element fixedly attached to said exterior surface of said cylindrical tube for heating said second length of said cylindrical tube and said drift gas in said space outside said cylindrical tube prior to entry into said drift region, said second housing having a collector positioned behind said aperture grid for collecting ions passing through said aperture grid, means for coupling a bias voltage to said aperture grid, means for coupling a signal external of said second housing indicative of said ions collected by said collector, and means for coupling power to said heating element.

* * * * *